US007141541B1

(12) United States Patent
Proud et al.

(10) Patent No.: US 7,141,541 B1
(45) Date of Patent: Nov. 28, 2006

(54) USE OF PEPTIDES

(75) Inventors: Christopher Gregory Proud, Dundee (GB); Terrence Patrick Herbert, Dundee (GB); David Philip Lane, Dundee (GB); Robin Fahraeus, Dundee (GB)

(73) Assignee: University Court of the University of Dundee (GB)

( * ) Notice: Subject to any disclaimer, the term of this patent is extended or adjusted under 35 U.S.C. 154(b) by 654 days.

(21) Appl. No.: 10/019,198

(22) PCT Filed: Jun. 21, 2000

(86) PCT No.: PCT/GB00/02414

§ 371 (c)(1), (2), (4) Date: Jun. 19, 2002

(87) PCT Pub. No.: WO00/78803

PCT Pub. Date: Dec. 28, 2000

(30) Foreign Application Priority Data

Jun. 21, 1999 (GB) .................................. 9914480.0

(51) Int. Cl.
*A61K 38/00* (2006.01)
*A61K 49/00* (2006.01)
(52) U.S. Cl. .......................................... 514/2; 530/300
(58) Field of Classification Search ............... 514/2; 530/300
See application file for complete search history.

(56) References Cited

U.S. PATENT DOCUMENTS 6,610,508 B1 * 8/2003 Hentze et al. ............. 435/69.1

FOREIGN PATENT DOCUMENTS

| WO | WO 94/18345 | 8/1994 |
| WO | WO 96/13614 | 5/1996 |
| WO | WO 98/39357 | 9/1998 |

OTHER PUBLICATIONS

Haghighat et al. (1996) The eIF4G-eIF4E complex is the target for direct cleavage by the rhinovirus 2A proteinase, J. Virol. vol. 70, No. 12, pp. 8444-8450.*
De Benedetti, et al., "Overexpression of eukaryotic protein synthesis initiation factor 4E in HeLa cells results in aberrant growth and morphology," *Proc. Natl. Acad. Sci. USA* 87: 8212-8216 (Nov. 1990).
Dostie, et al., "Nuclear Eukaryotic Initiation Factor 4E (eIF4E) Colocalizes with Splicing Factors in Speckles," *The Journal of Cell Biology* 148(2): 239-245 (2000).
Fletcher, et al., "4E Binding Proteins Inhibit the Translation Factor eIF4E without Folded Structure," *Biochemistry* 37: 9-15 (1998).
Flynn, et al., "Insulin-stimulated phosphorylation of initiation factor 4E is mediated by the MAP kinase pathway," *Federation of European Biochemical Societies* 389: 162-166 (1996).

Fukuchi-Shimogori, et al., "Malignant Transformation by Overproduction of Translation Initiation Factor eIF4G," *Cancer Research* 57: 5041-5044 (1997).
Green, et al., "Mitochondria and Apoptosis," *Science* 281: 1309-1312 (1998).
Hentze, Matthias W., "eIF4G: A Multipurpose Ribosome Adapter?" *Science*, 275(Jan.): 500-501 (1997).
Kroemer, Guido, "The proto-oncogene Bcl-2 and its role in regulating apoptosis," *Nature Medicine* 3(6): 614-620 (1997).
Li, et al., "Clinical Outcome in Stage I to III Breast Carcinoma and eIF4E Overexpression," *Annals of Surgery* 227(5): 756-763 (1998).
Li, et al., "Overexpression of Eukaryotic Initiation Factor 4E (eIF4E) in Breast Carcinoma," *American Cancer Society* 79: 2384-2390 (1997).
Minamikawa, et al., "Mitochondrial Permeability Transition and Swelling Can Occur Reversibly without Inducing Cell Death in Intact Human Cells," *Experimental Cell Research* 246: 26-37 (1999).
O Nathan, et al., "Detection of the proto-oncogene eIF4E in surgical margins may predict recurrence in head and neck cancer," *Oncogene* 15: 579-584 (1997).
Okuno, et al., "Bcl-2 Prevents Caspase-independent Cell Death," *The Journal of Biological Chemistry* 273(51): 34272-34277.
Pyronnet, et al., "Human eukaryotic translation initiation factor 4G (eIF4G) recruits Mnk1 to phosphorylate eIF4E," *EMBO Journal*, 18(1): 270-279 (1999).
Rosenwald, et al., "Elevated Levels of Cyclin D1 Protein in Response to Increased Expression of Eukaryotic Initiation Factor 4E," *Molecular and Cellular Biology* Dec.: 7358-7363 (1993).
Rosenwald, et al., "Upregulation of protein synthesis initiation factor eIF-4E is an early event during colon carcinogenesis," *Oncogene* 18: 2507-2517 (1999).
Rousseau, et al., "The eIF4E-binding proteins 1 and 2 are negative regulators of cell growth," *Oncogene* 13: 2415-2420 (1996).
Shantz, et al., "Regulation of Ornithine Decarboxylase in a Transformed Cell Line That Overexpresses Translation Initiation Factor eIF-4E," *Cancer Research* 56: 3265-3269 (1996).
Sonenberg, et al., "The mRNA5' cap-binding protein eIF4E and control of cell growth," *Current Opinion in Cell Biology*, 10: 268-275 (1998).
Sonenberg, et al., "Translational control of apoptosis: An essential role for initiation factor 4E in preventing oncogene-dependent cell death," *Biology* 28 abstract (1997).

(Continued)

*Primary Examiner*—Jon Weber
*Assistant Examiner*—Samuel Wei Liu
(74) *Attorney, Agent, or Firm*—Myers, Bigel, Sibley & Sajovec

(57) ABSTRACT

We claim a therapeutic method of inducing programmed cell death comprising administering to a recipient a peptide of 10–25 amino acids, comprising the sequence: (KR)xxYxxx(F/Q)L(L/M) wherein x is any amino acid.

5 Claims, 12 Drawing Sheets

OTHER PUBLICATIONS

Susin, et al., "Molecular characterization of mitochondrial apoptosis-inducing factor," *Nature* 397: 441-446 (1999).

Wolf, et al., "Suicidal Tendencies: Apoptotic Cell Death by Caspase Family Preteinases," *The Journal of Biological Chemistry* 274(29): 20049-20052 (1999).

Xiang, et al., "BAX-induced cell death may not require interleukin 1β-converting enzyme-like proteases," *Proc. Natl. Acad. Sci. USA* 93: 14559-14563 (1996).

Polunovsky et al. Abstract. "Translational Control of Apoptosis: An Essential Rold for Initiation Factor 4E in Preventing Oncogene-Dependent Cell Death," *Proceedings of the American Association For Cancer Research Annual.* 1997, vol. 38, pp. 624.

Altmann et al. "A novel inhibitor of cap-dependent translation initiation in yeast: p. 20 competes with eIF4G for binding to eIF4E," *Embo Journal.* 1997, vol. 16, No. 5, pp. 1114-1121.

Lawrence, J.C. et al. "PHAS/4E-BPs as regulators of mRNA translation and cell proliferation." *Tibs Trends in Biochemical Science.* 1997, vol. 22, No. 9, pp. 345-349.

Renschler et al. "B-Lymphoma Cells Are Activated by Peptide Ligands of the Antigen Binding Receptor or by Anti-Idiotypic Antibody to Induce Extracellular Acidification," *Cancer Research.* Dec. 1, 1995, vol. 55, pp. 5642-5647.

\* cited by examiner h4g human eIF4G    B β <u>K K R Y D R E F L L G F</u> A A R Q I K I W F Q N R R M K W K K    SEQ ID NO: 7

S scrambled eIF4G    B β <u>F D L K F A</u> <u>L G R Y R A</u> <u>E K</u> R Q I K I W F Q N R R M K W K K    SEQ ID NO: 8

\-    no peptide rec 4E    recombinant human eIF4E

FIGURE 5

| | Peptide | | | | | | | | | | | | | | | |
|---|---|---|---|---|---|---|---|---|---|---|---|---|---|---|---|---|
| H | human eIF4G | B | β | β | K | K | R | Y | D | R | E | F | L | L | G | F | 413-424 SEQ ID NO: 1 |
| Y | yeast eIF4G | B | β | β | K | Y | T | Y | G | P | T | F | L | L | Q | F | 449-460 SEQ ID NO: 9 |
| W | wheat eIF4G | B | β | β | R | V | R | Y | S | R | D | Q | L | L | D | L | 62-73 SEQ ID NO: 2 |
| 1 | human 4E-BP1 | B | β | β | R | I | I | Y | D | R | K | F | L | M | E | C | 51-62 SEQ ID NO: 10 |
| 2 | human 4E-BP2 | B | β | β | R | I | I | Y | D | R | K | F | L | L | D | R | 51-62 SEQ ID NO: 11 |
| S | scrambled eIF4G | | | | | | | | | | | | | | | | |

FIGURE 6

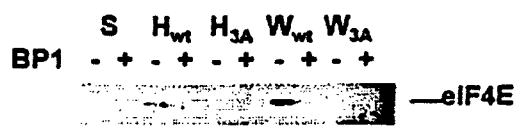

| 4G Peptide | | Sequence | |
|---|---|---|---|
| H$_{wt}$ | hu 4G$_{(413-424)}$ | K K R Y D R E F L L G F A A | SEQ ID NO: 12 |
| H$_{3A}$ | hu 4G$_{(413-424)YALALA}$ | K K R A D R E F A A G F A A | SEQ ID NO: 13 |
| W$_{wt}$ | wh 4G$_{(62-73)}$ | R V R Y S R D Q L L D L A A | SEQ ID NO: 14 |
| W$_{3A}$ | wh 4G$_{(62-73)YALALA}$ | R V R A S R D Q A A D L A A | SEQ ID NO: 15 |
| S | scrambled hu 4G | F D L K F A L G R Y R A E K | SEQ ID NO: 16 | all peptides biotinylated and linked to Penetratin™

+ Positive control
B human 4E-BP1
W wheat eIF4G$_{(62-73)}$

| Peptide | Concentration | | | |
|---|---|---|---|---|
| | 3 µM | 6 µM | 9 µM | 12 µM |
| hu 4G$_{(413-424)}$ | + | ++ | +++ | +++ |
| hu 4G$_{(413-424)Y416AL421AL422A}$ | - | - | - | - |
| wh 4G$_{(62-73)}$ | -/+ | + | ++ | +++ |
| wh 4G$_{(62-73)Y65AL70AL71A}$ | - | - | - | - |
| scrambled hu 4G | - | - | - | - |

MRC5 cells, 72 h serum-free growth, all peptides biotinylated and linked to Penetratin™

| | | | |
|---|---|---|---|
| Hu 4G | Human eIF4G Peptide (569-580)Wild Type | KKRYDREFLLGF | SEQ ID NO: 1 |
| Hu 4G YLL-AAA | Human eIF4G Peptide (569-580)Y572A L577A L578A | KKRADREFAAGF | SEQ ID NO: 17 |
| Hu 4G Y-A | Human eIF4G Peptide (569-580)Y572A | KKRADREFLLGF | SEQ ID NO: 18 |
| Hu 4G L-A | Human eIF4G Peptide (569-580)L577A | KKRYDREFALGF | SEQ ID NO: 19 |
| W4G | Wheat eIF4G Peptide (62-73)Wild Type | RVRYSRDQLLDL | SEQ ID NO: 2 |
| W4G YLL-AAA | Wheat eIF4G Peptide (62-73)Y65A, L70A, L71A | RVRASRDQAADL | SEQ ID NO: 20 |
| BP2 | Human 4E-BP2 Peptide (51-62)Wild Type | RIIYDRKFLLDR | SEQ ID NO: 11 |
| BP2 YLL-AAA | Human 4E-BP2 Peptide (51-62)Y54A, L59A, L60A. | RIIADRKFAADR | SEQ ID NO: 21 |
| BP1 | Human 4E-BP1 Peptide (51-62)Wild Type | RIIYDRKFLMEC | SEQ ID NO: 10 |
| BP1 YLM-AAA | Human 4E-BP1 Peptide (51-62)Y54A, L59A, M60A | RIIADRKFAAEC | SEQ ID NO: 22 |

(b)

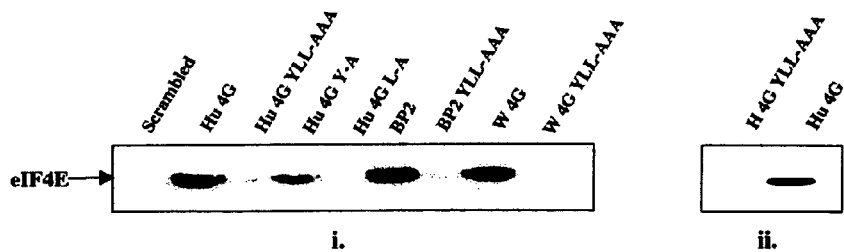

FIGURE 13
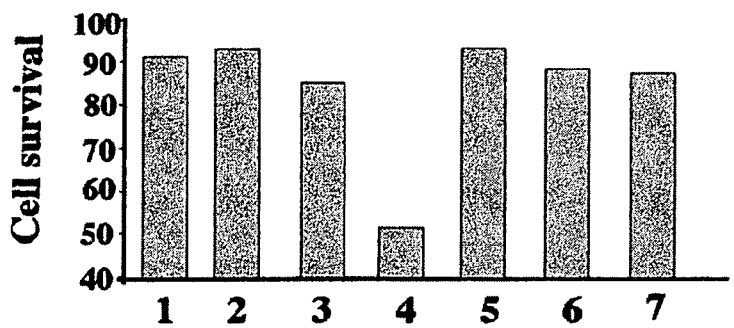
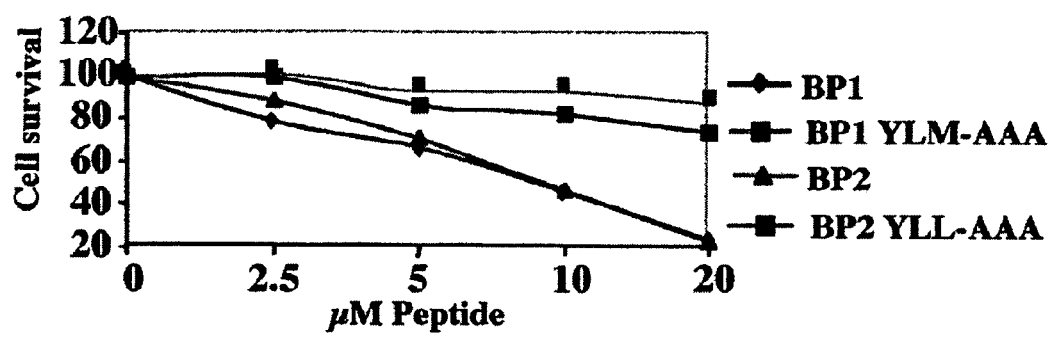
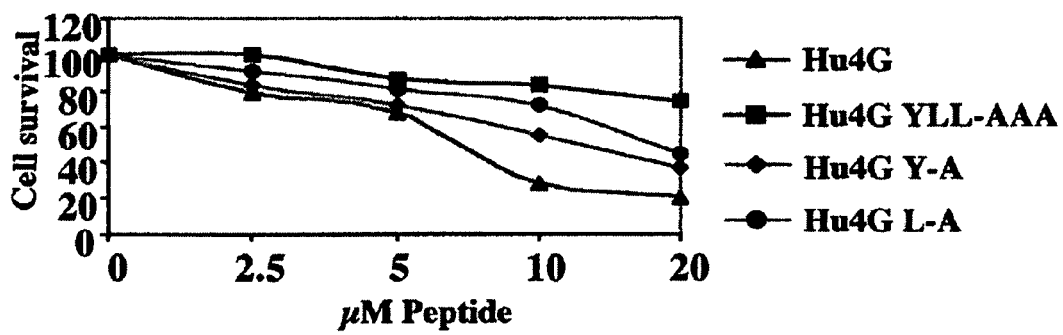
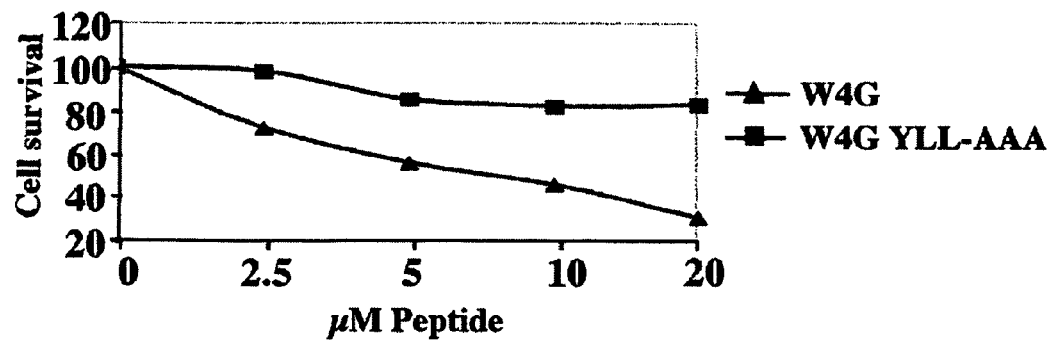

(a)

SEQUENCE LISTING

<160> NUMBER OF SEQ ID NOS: 22

<210> SEQ ID NO 1
<211> LENGTH: 12
<212> TYPE: PRT
<213> ORGANISM: Homo sapiens

<400> SEQUENCE: 1

Lys Lys Arg Tyr Asp Arg Glu Phe Leu Leu Gly Phe
1               5                   10

<210> SEQ ID NO 2
<211> LENGTH: 12
<212> TYPE: PRT
<213> ORGANISM: Triticum aestivum

<400> SEQUENCE: 2

Arg Val Arg Tyr Ser Arg Asp Gln Leu Leu Asp Leu
1               5                   10

<210> SEQ ID NO 3
<211> LENGTH: 10
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa can be Leu or Met

<400> SEQUENCE: 3

Arg Ile Ile Tyr Asp Arg Lys Phe Leu Xaa
1               5                   10

<210> SEQ ID NO 4
<211> LENGTH: 7
<212> TYPE: PRT
<213> ORGANISM: Artificial
<220> FEATURE:
<223> OTHER INFORMATION: Consensus peptide
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be Leu, Met or Phe

<400> SEQUENCE: 4

Tyr Xaa Xaa Xaa Xaa Leu Xaa
1               5

<210> SEQ ID NO 5
<211> LENGTH: 10
<212> TYPE: PRT
<213> ORGANISM: Artificial
<220> FEATURE:
<223> OTHER INFORMATION: Consensus peptide
<220> FEATURE:
<221> NAME/KEY: MISC_FEATURE
<222> LOCATION: (1)..(1)
<223> OTHER INFORMATION: Xaa can be Lys or Arg
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature

```
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be Phe or Gln
<220> FEATURE:
<221> NAME/KEY: MISC_FEATURE
<222> LOCATION: (10)..(10)
<223> OTHER INFORMATION: Xaa can be Leu or Met

<400> SEQUENCE: 5

Xaa Xaa Xaa Tyr Xaa Xaa Xaa Xaa Leu Xaa
1               5                  10

<210> SEQ ID NO 6
<211> LENGTH: 16
<212> TYPE: PRT
<213> ORGANISM: Artificial
<220> FEATURE:
<223> OTHER INFORMATION: Penetratin: membrane translocation peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 30
<212> TYPE: PRT
<213> ORGANISM: Homo sapiens

<400> SEQUENCE: 7

Lys Lys Arg Tyr Asp Arg Glu Phe Leu Leu Gly Phe Ala Ala Arg Gln
1               5                   10                  15

Ile Lys Ile Trp Phe Gln Asn Arg Arg Met Lys Trp Lys Lys
            20                  25                  30

<210> SEQ ID NO 8
<211> LENGTH: 30
<212> TYPE: PRT
<213> ORGANISM: Artificial
<220> FEATURE:
<223> OTHER INFORMATION: Scrambled eIF4G sequence

<400> SEQUENCE: 8

Phe Asp Leu Lys Phe Ala Leu Gly Arg Tyr Arg Ala Glu Lys Arg Gln
1               5                   10                  15

Ile Lys Ile Trp Phe Gln Asn Arg Arg Met Lys Trp Lys Lys
            20                  25                  30

<210> SEQ ID NO 9
<211> LENGTH: 12
<212> TYPE: PRT
<213> ORGANISM: Saccharomyces cerevisiae

<400> SEQUENCE: 9

Lys Tyr Thr Tyr Gly Pro Thr Phe Leu Leu Gln Phe
1               5                  10

<210> SEQ ID NO 10
<211> LENGTH: 12
<212> TYPE: PRT
<213> ORGANISM: Homo sapiens

<400> SEQUENCE: 10

Arg Ile Ile Tyr Asp Arg Lys Phe Leu Met Glu Cys
```

-continued 1 5 10

<210> SEQ ID NO 11
<211> LENGTH: 12
<212> TYPE: PRT
<213> ORGANISM: Homo sapiens

<400> SEQUENCE: 11

Arg Ile Ile Tyr Asp Arg Lys Phe Leu Leu Asp Arg
1 5 10

<210> SEQ ID NO 12
<211> LENGTH: 14
<212> TYPE: PRT
<213> ORGANISM: Homo sapiens

<400> SEQUENCE: 12

Lys Lys Arg Tyr Asp Arg Glu Phe Leu Leu Gly Phe Ala Ala
1 5 10

<210> SEQ ID NO 13
<211> LENGTH: 14
<212> TYPE: PRT
<213> ORGANISM: Artificial
<220> FEATURE:
<223> OTHER INFORMATION: Mutagenized human hu 4G sequence

<400> SEQUENCE: 13

Lys Lys Arg Ala Asp Arg Glu Phe Ala Ala Gly Phe Ala Ala
1 5 10

<210> SEQ ID NO 14
<211> LENGTH: 14
<212> TYPE: PRT
<213> ORGANISM: Triticum aestivum

<400> SEQUENCE: 14

Arg Val Arg Tyr Ser Arg Asp Gln Leu Leu Asp Leu Ala Ala
1 5 10

<210> SEQ ID NO 15
<211> LENGTH: 14
<212> TYPE: PRT
<213> ORGANISM: Artificial
<220> FEATURE:
<223> OTHER INFORMATION: Mutagenized wheat hu 4G sequence

<400> SEQUENCE: 15

Arg Val Arg Ala Ser Arg Asp Gln Ala Ala Asp Leu Ala Ala
1 5 10

<210> SEQ ID NO 16
<211> LENGTH: 14
<212> TYPE: PRT
<213> ORGANISM: Artificial
<220> FEATURE:
<223> OTHER INFORMATION: Scrambled hu 4G sequence

<400> SEQUENCE: 16

Phe Asp Leu Lys Phe Ala Leu Gly Arg Tyr Arg Ala Glu Lys
1 5 10

<210> SEQ ID NO 17
<211> LENGTH: 12
<212> TYPE: PRT
<213> ORGANISM: Artificial

```
<220> FEATURE:
<223> OTHER INFORMATION: Mutagenized human eIF4G peptide

<400> SEQUENCE: 17

Lys Lys Arg Ala Asp Arg Glu Phe Ala Ala Gly Phe
1               5                   10

<210> SEQ ID NO 18
<211> LENGTH: 12
<212> TYPE: PRT
<213> ORGANISM: Artificial
<220> FEATURE:
<223> OTHER INFORMATION: Mutagenized human eIF4G peptide

<400> SEQUENCE: 18

Lys Lys Arg Ala Asp Arg Glu Phe Leu Leu Gly Phe
1               5                   10

<210> SEQ ID NO 19
<211> LENGTH: 12
<212> TYPE: PRT
<213> ORGANISM: Artificial
<220> FEATURE:
<223> OTHER INFORMATION: Mutagenized human eIF4G peptide

<400> SEQUENCE: 19

Lys Lys Arg Tyr Asp Arg Glu Phe Ala Leu Gly Phe
1               5                   10

<210> SEQ ID NO 20
<211> LENGTH: 12
<212> TYPE: PRT
<213> ORGANISM: Artificial
<220> FEATURE:
<223> OTHER INFORMATION: Mutagenized wheat eIF4G peptide

<400> SEQUENCE: 20

Arg Val Arg Ala Ser Arg Asp Gln Ala Ala Asp Leu
1               5                   10

<210> SEQ ID NO 21
<211> LENGTH: 12
<212> TYPE: PRT
<213> ORGANISM: Artificial
<220> FEATURE:
<223> OTHER INFORMATION: Mutagenized human 4E-BP2 peptide

<400> SEQUENCE: 21

Arg Ile Ile Ala Asp Arg Lys Phe Ala Ala Asp Arg
1               5                   10

<210> SEQ ID NO 22
<211> LENGTH: 12
<212> TYPE: PRT
<213> ORGANISM: Artificial
<220> FEATURE:
<223> OTHER INFORMATION: Mutagenized human 4E-BP1 peptide

<400> SEQUENCE: 22

Arg Ile Ile Ala Asp Arg Lys Phe Ala Ala Glu Cys
1               5                   10
```

USE OF PEPTIDES

RELATED APPLICATION INFORMATION

This application claims priority under 35 U.S.C. § 371 from PCT Application No. PCT/GB00/02414 (published under PCT Article 21(2) in English), filed on Jun. 21, 2000, which claims the benefit of Great Britain Application Serial No. 9914480.0, filed on Jun. 21, 1999, the disclosures of which are incorporated by reference herein in their entireties.

The present invention relates to eukaryotic Initiation Factor 4G (eIF4GI, GII) and derivatives of eIF4E Binding Proteins (4-E-BP1, 2, 3, 4) that interact with it.

By way of introduction, the proposed mechanism of eukaryotic initiation factor complex formation will be described with reference to FIG. 1. The eIF4F complex is capable of initiating translation of 5' capped ($m^7G$) mRNAs[1]. This complex comprises eIF3, eIF4A, eIF4E and eIF4G (FIG. 1).

- eIF4G acts as a scaffold around which the other components are assembled.
- eIF4A is a helicase which is required to unwind regions of secondary structure in the 5'UTR of the mRNA.
- eIF3 is responsible for recruiting the 40S ribosomal sub-unit to the complex, interacting with both the 40S ribosomal sub-unit and eIF4G.
- eIF4E binds to both eIF4G and to the $m^7G$ cap at the 5' end of the mRNA, hence recruiting the 40S ribosomal sub-unit to the 5' untranslated region (UTR) of capped mRNAs.

eIF4E independent routes exist for the initiation of translation of some messages[2] (eg. via an internal ribosome entry site (IRES)). However, mRNAs containing a long 5' UTR are dependent on eIF4E for the recruitment of the eIF4F complex to the $m^7G$ cap, and the subsequent unwinding of the UTR by eIF4A. The critical role of eIF4E in cap dependent translation is attributed to the limited availability of the active species. eIF4E appears to be in limiting amounts relative to other eIF4F components[1], requires phosphorylation (by Mnk 1[3]) for maximum activity and can be excluded from the eIF4F complex by binding to a 4E-BP[4,5] (FIG. 2).

There is increasing evidence for a role of eIF4E in carcinogenesis. eIF4E induces cap dependent translation initiation in response to a number of mitogenic or proliferative stimuli[1,4,6]. Hormone and growth factor induced signal transduction can lead to hyperphosphorylation of 4E-BP by mTOR, resulting in the release of 4E-BP-bound eIF4E mTOR, resulting in the release of 4E-BP-bound eIF4E (FIG. 2). Similar stimuli also lead to activation of eIF4E via phosphorylation by Mnk-1. The resultant increase in eIF4E activity is required for the translation of several cap-dependent transcripts whose translation products are required for proliferation (eg. cyclin D1[7], Ornithine Decarboxylase (ODC)[3]).

The number of reports of increased levels of eIF4E in tumour samples is growing steadily[9,10], and in some cases eIF4E levels have been proposed to be a good indicator of prognosis[11,12]. Overexpression of eIF4E in cultured cell lines is reported to result in a transformed phenotype[13,14].

Overall these results have suggested that inhibiting eIF4E would result in inhibition of cap-dependent translation, resulting in little or no expression of mRNAs with strong eIF4E dependency for translation. This is expected to cause reduction in expression of several proteins involved in proliferation, and to reduce the transformed phenotype of some tumour cells.

It has also been reported that overexpression of eIF4E is capable of acting as an anti-apoptotic survival signal in fibroblasts undergoing Myc-induced apoptosis in serum-restricted conditions[15].

The variety of eIF4E interacting proteins (eIF4G and 4E-BPs) has allowed identification of a common motif, (K/R)xxYDRxFL(L/M), required for binding to eIF4E[4]. Subsequently a 20 amino acid fragment of human 4E-BP1 containing this motif was shown to be capable of binding to recombinant mouse eIF4E and inhibiting cap-dependent translation in an in vitro translation assay[16], presumably by disrupting the formation of the eIF4F complex.

The proposed approach was to use eIF4E-binding peptides (derived from eIF4G and 4E-BPs) to inhibit formation of the eIF4F complex and reduce cap-dependent translation (FIG. 3).

The present invention is based upon the observation that eIF4E binding peptides have been shown for the first time to induce programmed cell death. This observation is surprising given that the expected effect of such peptides was to reduce expression of several proteins involved in proliferation, resulting in growth inhibition of, or increased cytotoxicity to tumour cells. This surprising observation renders these peptides of utility in therapy.

Thus, in a first aspect the present invention provides the use of eIF4E binding agents, such as peptides or peptidemimetics in therapy, more particularly for the induction of programmed cell death. Particular peptides found to be capable of inducing programmed cell death include a sequence of human eIF4G$_{569-580}$, wheat eIF4G$_{62-73}$ and human eIF4E-BP(1&2)$_{51-62}$ and derivatives and fragments thereof. Numbering according to Accession numbers AF104913, M95746, NM_004095 and NM_004096 respectively.

Thus the peptides of use in the present invention include the sequences;

human eIF4G$_{569-580}$, KKRYDREFLLGF [SEQ ID NO: 1]

wheat eIF4G$_{62-73}$ RVRYSRDQLLDL [SEQ ID NO: 2] and, human eIF4E-BP(1&2)$_{51-60}$ RIIYDRKFL(L/M) [SEQ ID NO: 3], and variants or derivatives thereof. A consensus may be derived from the above three sequences.

Thus, in a further aspect the present invention provides use of a peptide comprising a sequence:

YxxxxLØ [SEQ ID NO: 4]

wherein x is a variable amino acid and Ø is Leu, Met or Phe; or a fragment or derivative thereof in therapy, more particularly for the induction of programmed cell death.

Alternatively the peptide may comprise the sequence: (K/R)xxYxxx(F/Q)L(L/M) [SEQ ID NO: 5]

It is to be understood that "K/R" refers to an amino acid which is either lysine (K) or arginine (R), "x" may be any of the 20 amino acids or may be a synthetic or unnatural amino acid, "F/Q" refers to an amino acid which is either phenylalanine (F) or glutamine (Q) and "L/M" refers to an amino acid which is either leucine (L) or methionine (M). The remainder of the sequence is understood to relate to the standard single letter symbol for amino acids.

Particular sequences may include

KKRYDREFLLGF [SEQ ID NO: 1] (human eIF4G$_{413-424}$),

RVRYSRDQLLDL [SEQ ID NO: 2] (wheat eIF4G$_{62-73}$) and

RIIYDRKFL(L/M) [SEQ ID NO: 3] (human eIF4E-BP$_{51-60}$).

The invention also relates to the use of fragments and derivatives of these peptides. Fragments are defined herein as any portion of the peptides described that substantially retain the activity of the parent peptide. Derivatives are defined as any modified forms of said peptides which also substantially retain the activity of the parent peptide. Such derivatives may take the form of amino acid substitutions which may be in the form of like for like eg. a polar amino acid residue for another polar residue or like for non-like eg. substitution of a polar amino acid residue for a non-polar residue as discussed in more detail below.

Thus, the present invention further provides derivatives of the sequences disclosed above for use in the induction of cell death.

Replacement amino acid residues may be selected from the residues of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. The replacement amino acid residue may additionally be selected from unnatural amino acids. Within the above definitions of the peptide carrier moieties of the present invention, the specific amino acid residues of the peptide may be modified in such a manner that retains their ability to induce programmed cell death, such modified peptides are referred to as "variants". Thus, homologous substitution may occur i.e. like-for-like substitution such as basic for basic, acidic for acidic, polar for polar, etc. Non-homologous substitution may also occur ie. from one class of residue to another or alternatively involving the inclusion of unnatural amino acids such as ornithine (O), diaminobutyric acid (B), norleucine (N), pyriylalanine, thienylallanine, naphthylalanine and phenylglycine and the like. Within each peptide carrier moiety more than one amine acid residue may be modified at a time, but preferably when the replacing amino acid residue is alanine, less than 3.

As used herein, amino acids are classified according to the following classes;

basic; H,K,R acidic; D,E polar; A,F,G,I,L,M,P,V,W non-polar; C,N,Q,S,T,Y, (using the internationally accepted amino acid single letter codes)

and homologous and non-homologous substitution is defined using these classes. Thus, homologous substitution is used to refer to substitution from within the same class, whereas non-homologous substitution refers to substitution from a different class or by an unnatural amino acid.

In general, the term "peptide" refers to a molecular chain of amino acids with the defined biological activity. If required, it may be modified in vivo and/or in vitro, for example, by glycosylation, myristoylation, amidation, carboxybolation or phosphorylation. Thus inter alia peptides, oligopeptides and polypeptides are included. The peptides disclosed herein may be obtained, for example, by synthetic or recombinant techniques known in the art.

The term also extends to cover, for example, polypeptides which contain any of the above disclosed sequences and, in particular, wherein biological activity, that is, the polypeptide is capable of binding to eIF4E protein, is retained. Typically the length of the peptides of the present invention are between 7–25 amino acids in length, more preferably 10–20 amino acids in length.

In a further aspect the present invention provides use of a peptide comprising sequence:

YxxxxLØ [SEQ ID NO: 4] wherein x is a variable amino acid and Ø is Leu, Met or Phe;

or fragment or derivate thereof in the manufacture of a medicament for therapy, more particularly for inducing cell death.

In particular, the peptide is used to induce the cell death in tumour cells.

In yet a further aspect, the present invention provides a polynucleotide fragment encoding a peptide comprising sequence:

YxxxxLØ [SEQ ID NO: 4] wherein x is a variable amino acid and Ø is Leu, Met or Phe.

"Polynucleotide fragment" as used herein refers to polymeric form of nucleotides of any length, both to ribonucleic acid sequence and to deoxyribonucleic acid sequences. In principal, this term refers to the primary structure of the molecule, thus this term includes double stranded and single stranded DNA, as well as double and single stranded RNA, and modifications thereof.

As described above, the presence of a peptide comprising the above sequences can induce programmed cell death (apoptosis) in mammalian cells. The peptides of the present invention therefore have utility in treating diseases associated with undesirable cell proliferation/neoplasia. In particular the peptides have utility as anticancer or antitumour agents. Therefore, it may be desirable to direct the peptides to the site of action ie. the tumour. Thus, in the case of peptides, they may be conjugated to or associated with cell and/or tumour targeting agents, or in the case of the polynucleotide fragments provided as an expression cassette which comprises a polynucleotide sequence which encodes any of the above disclosed peptides, and a tumour-specific inducible promoter which would allow expression of the peptide of the present invention only in tumour cells. The peptides of the present invention may also be conjugated or associated with agents designed to facilitate uptake into cell such as transport peptides eg. penetratin.

The present invention also relates to the use of peptidemimetics which bind eIF4E and function to induce programmed cell death. Such peptidemimetics are generally small molecules which function in the same manner as the peptides disclosed herein.

These and other aspects of the present invention will become apparent from the following description when taken in combination with the accompanying Figures, in which:

FIG. 5 illustrates the binding of human, yeast, wheat and scrambled eIF4G, human 4E-BP1 and 4E-BP2 to eIF4E and the sequences employed;

FIG. 6 illustrates human 4E-BP1 competing with eIF4G peptides for the binding of eIF4E and the sequences employed;

Figure 14:
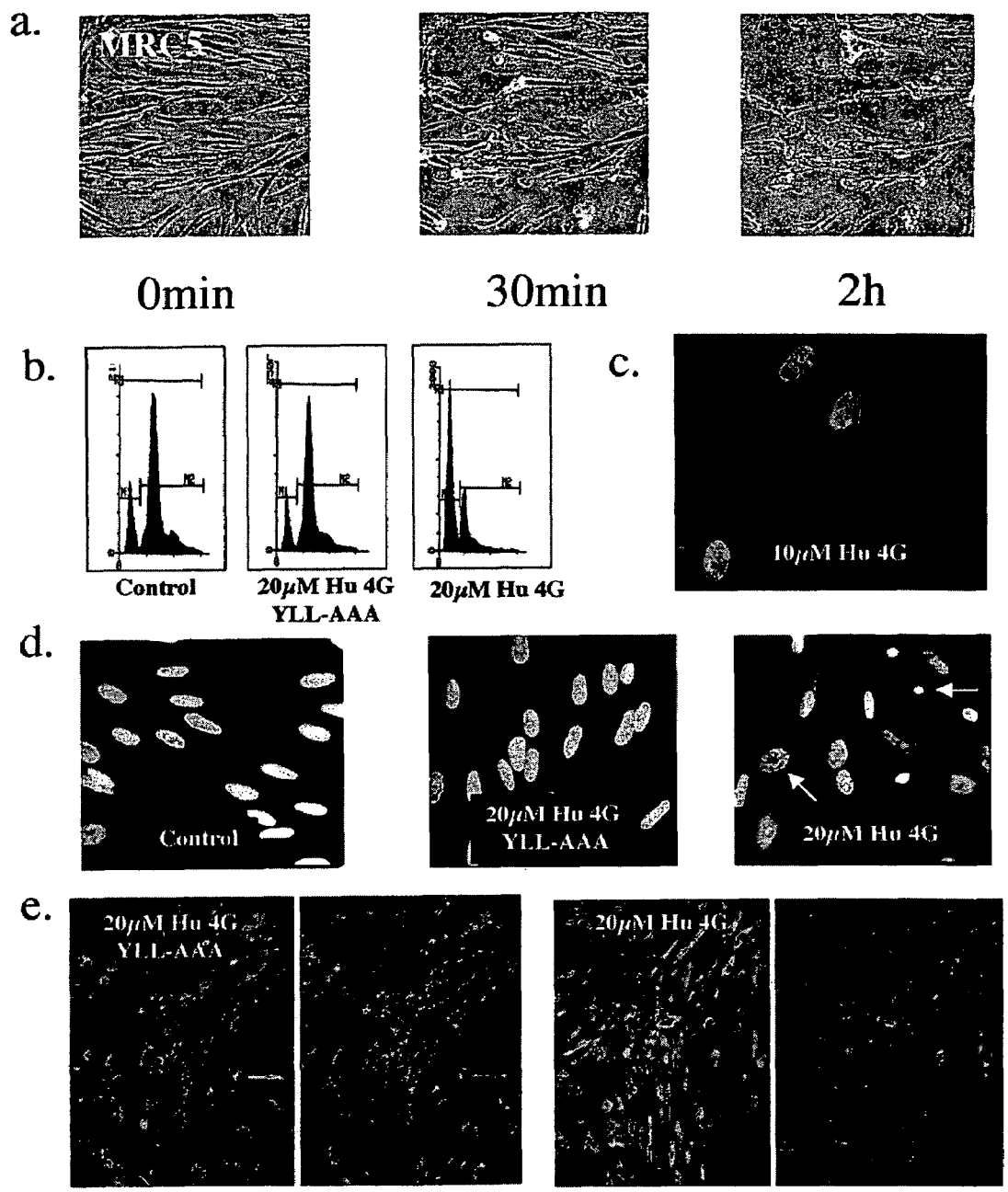
Figure 15:
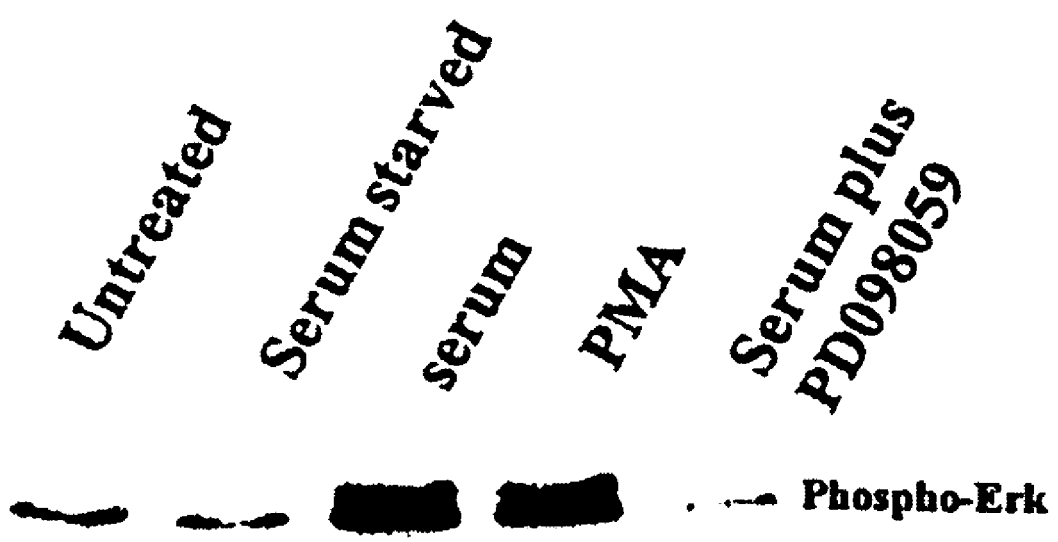
Figure 16:
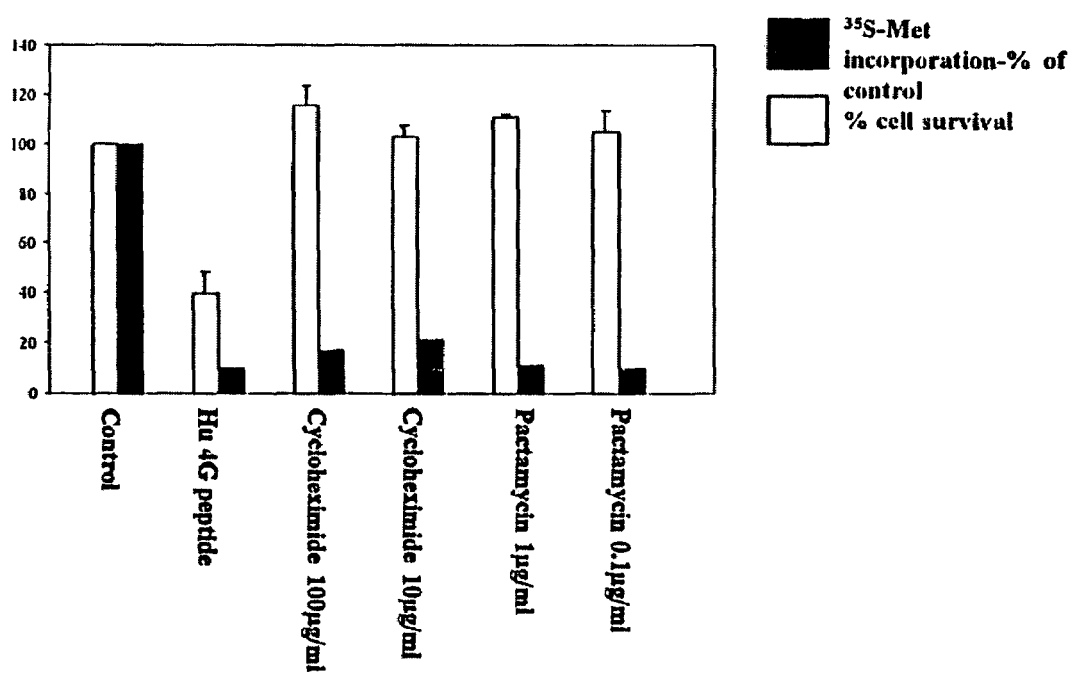
Figure 16:
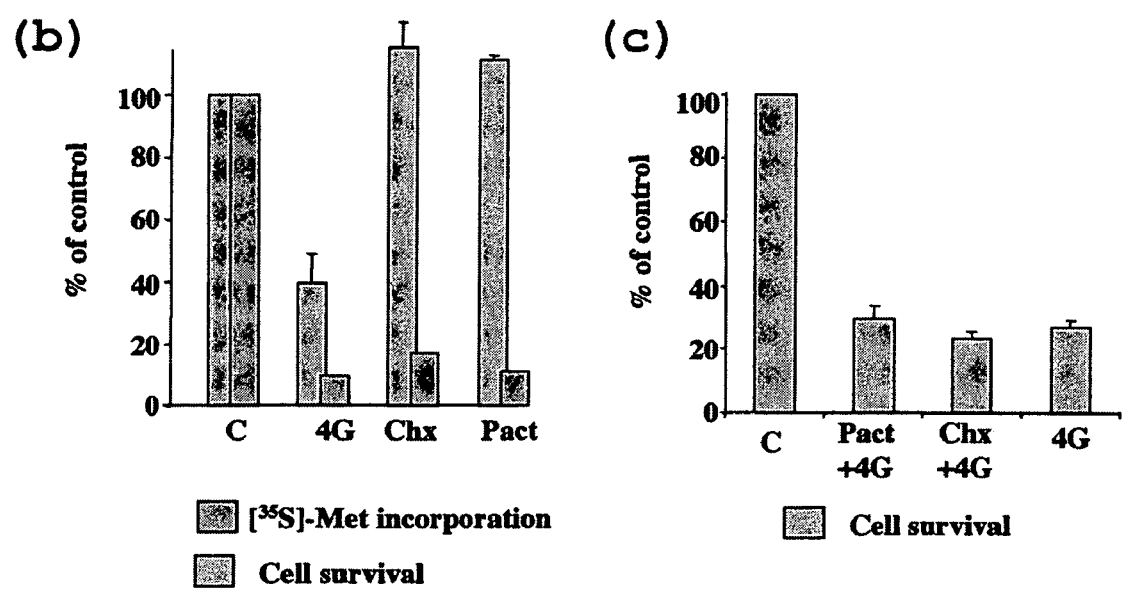

FIG. 12 illustrates that eIF4E-binding peptides leads to rapid, dose-dependent, cell death. a). Sequences of biotinylated, penetratin-linked peptides. U=Norvaline, a substitution for cysteine. Conserved residues that are important in binding to eIF4E are underlined. b). In vitro binding assay. i) 1 µg recombinant eIF4E was incubated with 0.2 mM biotinylated peptides in a total volume of 50 µl wash buffer (1×PBS/250 mM Kcl) for 1 h at 4° C. ii) 0.2 mM Hu4G or Hu4G YLL-AAA was incubated with 200 µg MRC5 cell lysate for 1 h at 4° C. in a total volume of 50 µl wash buffer. In all cases the biotinylated peptides and associated proteins were pulled down using streptavidin agarose. The proteins were separated by SDS PAGE and subjected to Western blotting using anti-eIF4E antibody. Detection was by ECL;

FIGS. 13a–d are graphs showing cell survival (% of control, untreated cells) as measured by MTT assay. a) Lane 1: 10 µM BP2 peptide added to serum-fed cells or Lane 2, 3, 4: 10 µM BP2 peptide added to 24 h, 48 h or 72 h serum-starved cells respectively. Lane 5: 10 µM BP2 YLL-AAA added to 72 h serum starved cells. Lane 6: 72 h serum starved cells incubated in 10% serum for 1 h prior to addition to 10 µM BP2 peptide. Lane 7: 72 h serum starved cells incubated with 100 µg/ml cycloheximide followed by a 1 h incubation with 10% serum prior to the addition of 10 µM BP2 peptide. In all cases the cells were then further incubated for 1 h in 0.1 mg/ml MTT. Cells were lysed in DMSO and absorbance was measured at 570 mm. b–d) Varying concentrations of peptides were added to 72 h serum starved MRC5 cells. After 30 min incubation the cells were then further incubated for 1 h in 0.1 mg/ml MTT. Cells were lysed in DMSO and absorbance was measured at 570 nm. All these results are representative of three separate experiments;

FIG. 14 illustrates that cell death induced by eIF4E-binding peptides shows characteristics of apoptosis. a) Time lapse images of serum-starved MRC5 cells treated with 10 µM Hu4G peptide for the indicated times. b) FACS analysis of MRC5 cells treated with 20 µM Hu4G or Hu4G YLL-AAA for 40 min. c) TUNEL analysis using the "In situ cell death detection kit" (Boehringer Mannheim). MRC5 cells were incubated with 10 µM Hu4G peptide for 10 min. Cells visualised with fluorescein by fluorescence microscopy. No signal was observed in untreated cells or cells treated with 10 µM Hu4G YLL-AAA peptide (results not shown). 80% of cells incubated with the 10 µM Hu4G peptide fluoresced positive. d) Images of DAPI-stained MRC5 cells incubated with either 20 µM Hu4G or Hu4G YLL-AAA peptide for 40 min. Arrows indicate the position of a cell with either a condensed nucleus (top right) or a nucleus with a punctate appearance (bottom left). e) Visualisation of effects on the MPT. Serum-starved MRC5 cells were loaded with 0.1 µM JCl for 30 min prior to addition of 10 µM peptide. Changes in mitochondrial permeability were viewed by laser scanning confocal microscopy (krypton/argon laser) using identical setting. Green channel: excitation 488 nm/emission 522 nm. Red channel: excitation 568 nm/emission 585 nm. Channels were collected separately to avoid cross over. Images were taken 5 min after addition of the peptide;

FIG. 15 illustrates that the acute activation of MAP kinase protects cells from 4E-binding peptide induced cell death; and FIG. 16 illustrates that eIF4E binding peptide cell death is not through eIF4E's known role in mRNA translation. a) 72 h serum-starved MRC5 cells were treated with 100 µg/ml and 10 µg/ml cylcoheximide, 1 µg/ml and 0.1 µg/ml pactamycine or 10 µM Hu4G peptide for 2 h prior to a MTT assay. Cells were pulsed labelled with [$^{35}$S]methionine for 30 min after addition of the inhibitors/peptide. The incorporation of [$^{35}$S]methionine into protein was determined following hot trichloroacetic acid precipitation. b) 72 h serum-starved MRC5 cells were treated with 100 µg/ml cycloheximide (Chx), 1 µg/ml pactamycine (Pact) or c) MRC5 cells which had been starved of serum for 72 h were pre-incubated with 100 µg/ml cycloheximide or 1 µg/ml pactamycine for 30 min prior to addition of 10 µM Hu4G peptide. Cells were then further incubated for 1.5 h prior to a MTT assay. Results from three independent experiments (+/− SEM).

EXAMPLES

Abbreviations.

Amino acid and peptide nomenclature conforms to IUPAC-IUB rules (Eur. J. Biochem. 1984, 138, 9–37). Other abbreviations: Ahx, 6-aminohexanoyl; APase, alkaline phosphatase; DE MALDI-TOF MS, delayed-extraction matrix-assisted laser desorption ionisation time-of-flight mass spectrometry; DIEA, N,Ndiisopropylethylamine; PBS, phosphate-buffered saline (10 mM phosphate, 150 Mm NaCl, pH 7.4); PyBOP, Benzotriazole-1-yl-oxy-tris-pyrrolidino-phosphonium hexafluorophosphate; RP-HPLC, reversed-phase high-performance liquid chromatography; TFA, trifluoroacetic acid.

Material and Methods

General

The peptide deprotection/cleavage mixture used throughout was as follows: 0.75:0.5:0.5:0.25:10 (W/V/V/V/V) PhOH, H$_2$O, PhSMe, 1,2-ethanedithiol, TFA (Beavis, R. C., et al., (1992) Organic Mass Spectrometry 27, 156–158). Analytical and preparative RP-HPLC was performed using Vydac 218TP54 (4.6×250 mm) and 218TP1022 (22×250 mm) columns, respectively. Flow rates of 1 mL/min for analytical runs and 9 mL/min for preparative work were used (at 25° C.). Gradient elution with increasing amounts of MeCN in H$_2$O (containing 0.1% TFA) over 20 min (anal.) and 40 min (prep.) was performed. Eluants were monitored at X=200–300 nm. Peptide samples were also analysed by DE MALDI-TOF mass spectrometry (ThermoBioAnalysis Dynamo instrument). An α-cyano-4-hydroxycinnamic acid matrix (Beavis, R. C. et al., (1992) Organic Mass Spectrometry 27, 156–158) was used and the appropriate m/z range was calibrated using authentic peptide standards in the m/z range 1,000–2,600.

Simultaneous Multiple Synthesis of Peptides

Peptides were synthesisted using a Multipin Peptide Synthesis Kit (Chiron Technologies Pty. Ltd., Clayton, VIC, Australia). Peptide chains were assembled on "Macro Crowns" (SynPhase HM Series I, Rink Amide Linker; 5.3 µmol/crown) using Fmoc-amino acids (100 mM in DMF) and PyBOP/HOBt)/DIEA (1:1:1,5) coupling chemistry. The amino acid side-chain protecting groups were 2,2,5,7,8-pentamethylchroman-6-sulphonyl (Arg), trityl (Asn and Gln) and t-butyloxycarbonyl (Lys and Trp). Activated amino acid solutions were dispensed using a PinAID device (Chiron Technologies). Coupling reactions were allowed to proceed for a minimum of 4 h. All other chain assembly manipulations, including repetitive deprotection reactions (20% piperidine in DMF) and washing cycles (DMF and MeOH), were carried out according to procedures set out in the kit manual. After coupling and deprotection of the N-terminal βAla residues, (+)-biotin (300 mM in DMF) was coupled (chemistry as above for amino acids) during 4 h. After washing and drying, the "Macro Crowns" were removed from the synthesis device and placed into 10 mL capped polypropylene tubes. To each tube was added 1.5 mL of cleavage/deprotection mixture. After 2 h, the "Macro Crowns" were removed and washed with 0.5 mL each of neat TFA. To each tube containing the combined cleavage mixtures and washings $Et_2O$ (8 mL) was added. After cooling to 4° C., the precipitated peptides were collected by centrifugation (4 min at 5,000 r.p.m.) and decantation. The pellets were resuspended in $Et_2O$ (5 mL/tube). The suspensions were again cooled and the peptides isolated as before. The washing process was repeated once more before the crude peptides were dried in vacuo.

The crude peptides were redissolved in 0.1% aq TFA using sonication (2 mL/sample) and were applied to primed (MeOH then 0.1% aq TEA) solid-phase extraction cartridges (Merck LiChrolut RP-18, 500 mg). These were successively washed (2×2 mL 0.1% aq TFA each) and eluted (2 mL 0.1% TFA in 6:4 $MeCN/H_2O$). The eluates were evaporated to dryness by vacuum centrifugation.

Results and Discussion

The importance of eIF4E in translational regulation and cell growth is underscored by observations which show that overexpression of eIF4E leads both to increases in protein synthesis and to cellular transformation in human and mouse cells (17,18). The mechanism by which eIF4E overexpression leads to cell transformation is poorly understood. However, it is thought to be through the elevated translation of growth related mRNAs, which are normally translationally repressed (19). In order to study directly the role of eIF4E in cell transformation, a series of experiments were carried out.

Figure 4:
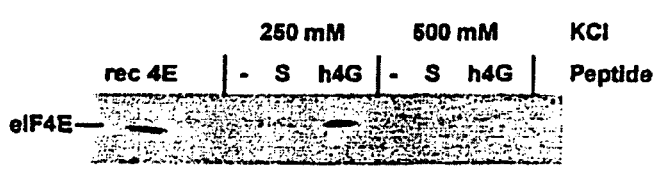
FIG. 4 illustrates the binding of human eIF4G-Penetratin conjugate to eIF4E and the sequences employed.

Human $eIF4G_{(413-424)}$ was conjugated to Penetratin, a known cell membrane translocation peptide of sequence RQIKIWFQNRRMKWKK [SEQ ID NO: 6] (see patent EP485578). Description of its synthesis and coupling to other peptides may be found in U.S. Pat. No. 5,888,762. The human $eIF4G_{(413-424)}$-Penetratin conjugate was found to bind recombinant human eIF4E in vitro (see FIG. 4). Surprisingly, wheat $eIF4E_{(62-73)}$ bound to and pulled down more recombinant human eIF4F in vitro than human $eIF4G_{(569-580)}$ did (see FIG. 5). It was also observed that recombinant human 4E-BP1 competed with either human $eIF4G_{(569-580)}$ or wheat $eIF4G_{(62-73)}$ for binding of recombinant human eIF4E in vitro (see FIG. 6).

Figures 7, 8:
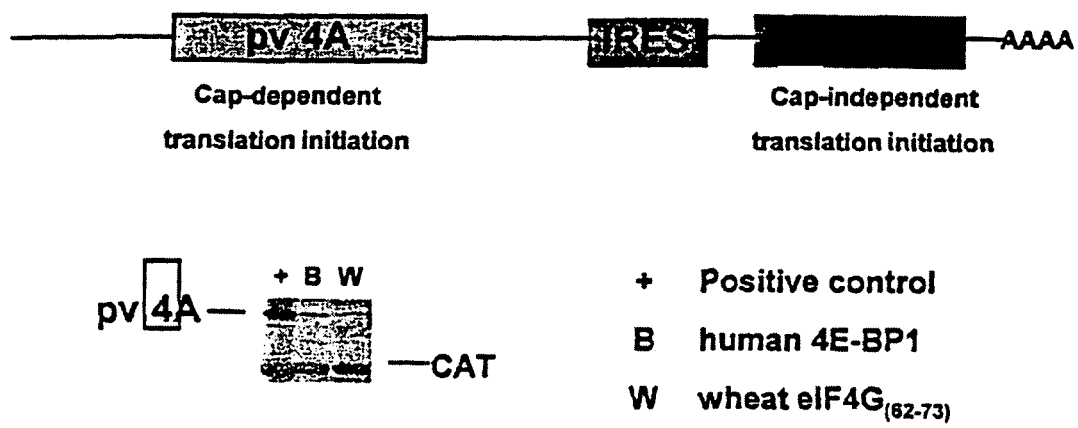
FIG. 7 illustrates wheat eIF4G$_{(62-73)}$ inhibiting cap-dependent translation initiation.
FIG. 8 is a table illustrating the induction of apoptosis by eIF4G peptides in MRC5 cells.

Wheat $eIF4G_{(62-73)}$ was found to inhibit cap-dependent translation initiation, but not cap-independent translation initiation in vitro (see FIG. 7). However, inhibition of cap dependent translation by eIF4G peptides was not detected in cultured mammalian cells. Furthermore, no inhibition of general translation by peptides from eIF4G or 4E-BP was detected in cultured mammalian cells.

Human $eIF4G_{(569-580)}$-Penetratin exhibited a cytotoxic or cytostatic effect on selected cell lines (HaCaT cells, no effect observed with short treatment (<24 h with 20 μM) but treatment of 60 h serum starved cells began to die within 15 minutes of peptide treatment. Furthermore, human $eIF4G_{(413-424)}$-Penetratin and wheat $eIF4G_{(62-73)}$-Penetratin caused rapid cell death (possibly by apoptosis) in serum starved cell lines (see FIG. 8).

Figure 1:
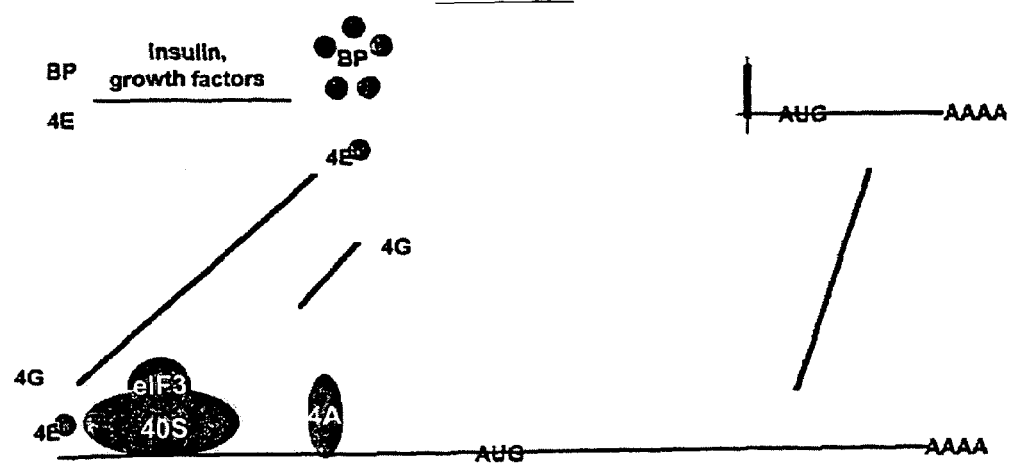
FIGS. 1 to 3 are diagrams illustrating the interaction of eIF4G and eIF4E.
Figure 2:
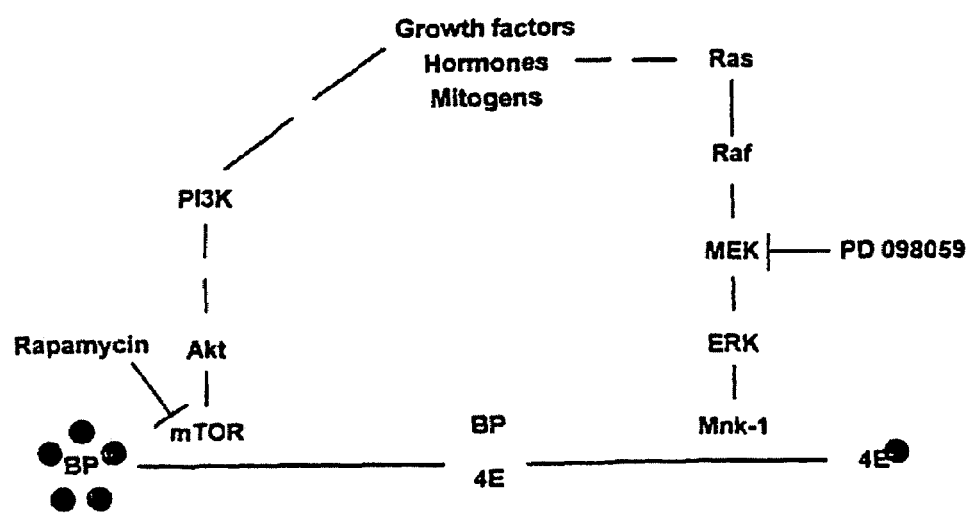
Figure 3:
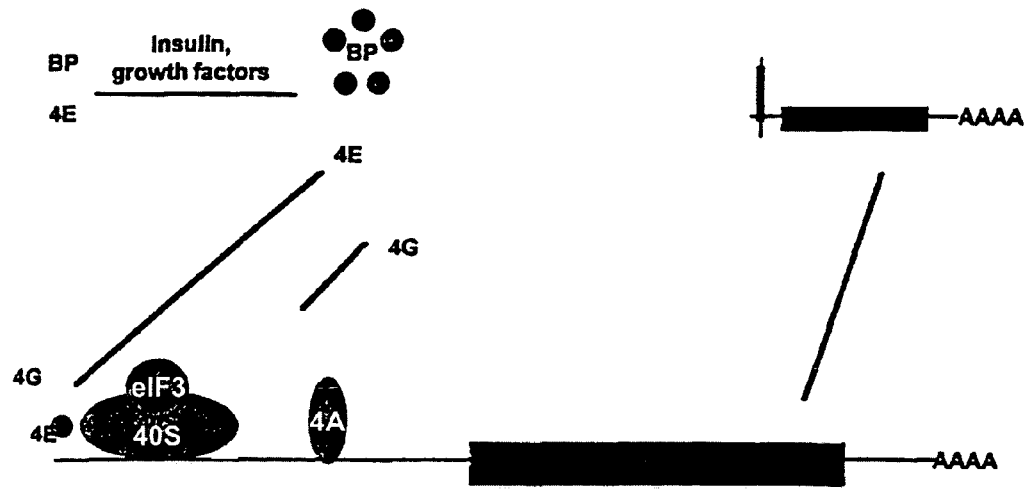
Figure 9:
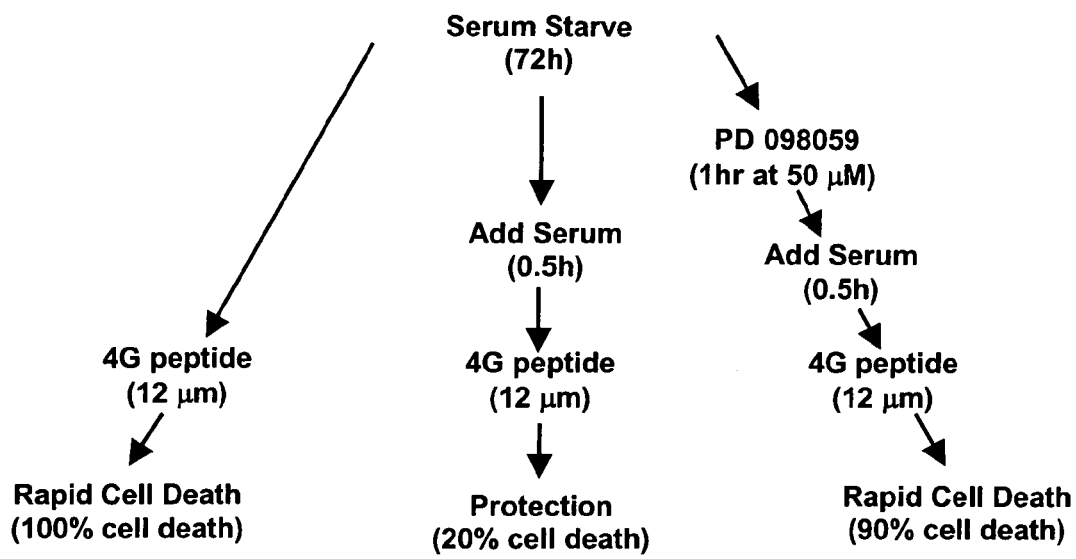
FIG. 9 is a summary of the results of inhibition of eIF4G$_{(413-424)}$-induced apoptosis.
Figure 10:
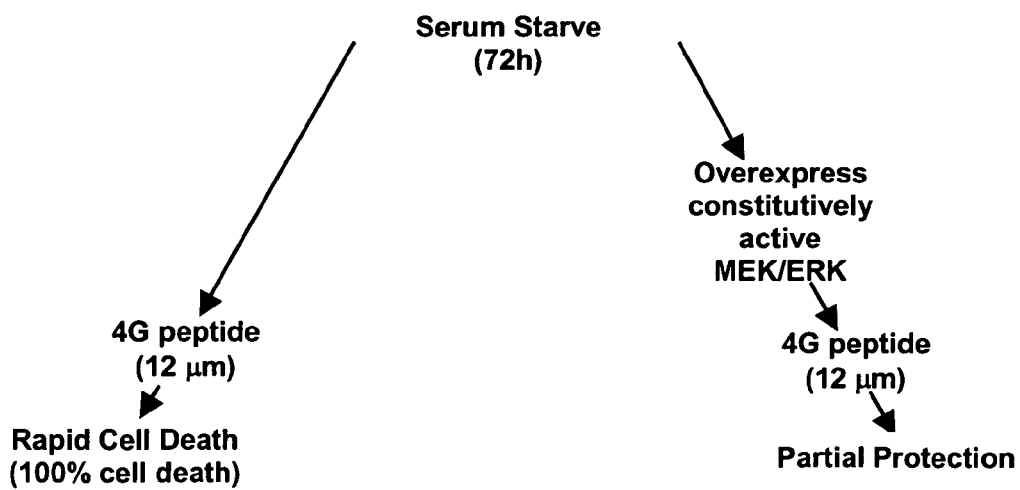
FIG. 10 is a summary of the results of inhibition of eIF4G$_{(569-580)}$-induced apoptosis in MRC5 cells overexpressing constitutively active MEK/ERK.
Figure 11:
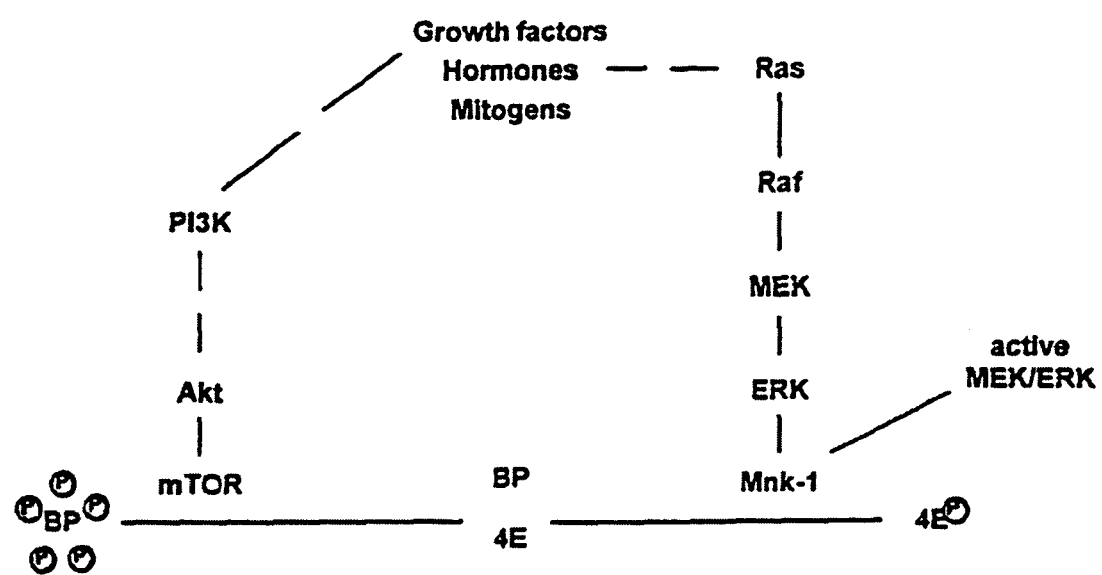
FIG. 11 is a diagram illustrating the interaction of eIF4G and eIF4E.

Resistance to Human $eIF4G_{(569-580)}$-Penetratin and wheat $eIF4G_{(62-73)}$-Penetratin resulted from limited serum treatment (see FIGS. 9 & 2). However, this serum induced resistance could be inhibited by pre-treatment with MEK inhibitor PD 098059 (see FIGS. 9 & 2). Furthermore, serum induced resistance could be mimicked by the overexpression of a constitutively active MEK/ERK fusion (see FIGS. 10 & 11). However, the serum induced resistance of cell lines was overcome using an increased concentration of peptide (72 h serum-starved MRC5 cells died rapidly with addition of 10 μM 4G peptides; cells grown in 10% serum show similar biological effect with 40 μM 4G peptides; however, control peptides (triple Ala substitution) were not cytotoxic at 40 μM).

Conservation of structure activity relationship (SAR) was found in wheat and human 4G peptides and human 4E-BP peptides in binding assay, functional cell free assay and cell culture assays.

In order to study directly the role of eIF4E in cell transformation, a series of biotinylated synthetic peptides (Peptides synthesised by Cyclacel) corresponding to the eIF4E interacting domain (binding motif) of human eIF4G, and wheat eIF4G and alanine substituted peptides thereof were synthesised (see FIG. 12a) and tested for their capacity to interact with $^{35}$S-Met labelled in vitro translated human eIF4E (NB. Peptides BP1 and BP1 YLM-AAA were not biotinylated). Peptides were coupled to streptavidin coated agarose beads by a N-terminus linked biotin group and washed in PBS/0.2% Tween 3× before being incubated for 1 hour at +4° C. with in vitro translated human eIF4E. Beads were washed as above and boiled for 5 min. in SDS loading buffer before the peptide bound proteins were separated on a 10% SDS gel. The bands were visualised by autoradiography.

Triple alanine substituted derivatives such as Human $eIF4G_{(569-580)Y416A L421A L422A}$ (see FIG. 8) were found not to inhibit cap-dependent translation initiation in vitro. However, 4G peptides containing specific single alanine substitutions (such as Human $eIF4G_{(569-580)Y416A}$) partially inhibited cap-dependent translation initiation in vitro.

Triple alanine substituted derivatives such as Human $eIF4G_{(569-580)Y416A L421A L422A}$-Penetratin did not cause the observed biological effect (apoptosis) in MRC5 cells (see FIG. 8). However, 4G peptides containing specific single alanine substitutions (such as Human $eIF4G_{(569-580)Y416A}$-Penetratin) had an intermediate biological effect on cultured mammalian cells, ie. reduced rate and extent of cell killing was observed.

The three different wild type peptides were shown to interact with human eIF4E and the H4G Y-A substitution had a lower binding affinity (see FIG. 12b(i)). Scrambled human eIF4G peptide, the triple alanine human eIF4G peptide and the triple alanine wheat eIF4G peptides as well as the single H4G L-A did not interact with eIF4E. The Hu4G peptide also bound eIF4E in cell lysates whereas the Hu4G YLL-AAA variant did not (see FIG. 12b(ii)).

To investigate the effect of eIF4E binding peptides (eIF4G, BP1 and BP2) in living cells, 10 μM of the eIF4E binding peptide BP2 was incubated with serum-deprived or serum-fed MRC5 cells. Un-expectedly, the addition of the BP2 peptide to 72 h serum-starved MRC5 cells led to rapid cell death (within 1 h) (FIG. 13a, lane 4). In contrast, serum-fed cells were insensitive to the effect of the BP2 peptide at this concentration (FIG. 13a, lane 1). Incubation of either serum-fed or serum-starved MRC5 cells with the triple alanine substitution peptide, BP2 YLL-AAA, had no significant effect on cell viability (FIG. 13a, lane 5 and data not shown). The sensitivity of the cells to the effect of the peptide increased with the length of time the cells had been deprived of serum, with maximal effects observed by 72 h serum starvation (FIG. 13a, lanes 1–4). All subsequent experiments were therefore performed in cells deprived of serum for 72 h. Re-addition of 10% serum for one hour to 72 h serum-starved cells protected them from the effects of the peptide (FIG. 13a, lane 6). This protective effect could not be inhibited by pre-incubation of the cells with cycloheximide, an inhibitor of general mRNA translation (FIG. 13a, lane 7). This indicates that serum protects against peptide-induced cell death through a post-translational modification rather than by inducing synthesis of new proteins, e.g., cell survival proteins. To investigate further the effect of eIF4E-binding peptides, serum-starved MRC5 cells were incubated with various concentrations of the BP2, BP1, Hu4G and W4G peptides (FIGS. 13b,c,d). Each of these peptides elicited rapid, dose-dependent, cell death (within 30 min using 20 μM peptide and 1 h for 10 μM), whereas the addition of the triple alanine substitution peptides, which are unable to bind eIF4E, had no significant effect on cell viability (FIGS. 13b,c,d). The singly alanine-substituted peptide, Hu4G Y-A, which has reduced ability to bind eIF4E in vitro, also had a reduced capacity to induce cell death (FIG. 13c). Another single alanine substitution peptide, Hu4G L-A, which was unable to bind eIF4E in-vitro, had a severely reduced ability to induce cell death up to 10 μM (FIG. 13c). However, upon addition of higher concentrations (20 μM), this peptide could induce cell death probably indicating some residual low binding affinity for eIF4E not detected in the pull-down assay (FIG. 13c). All the peptides which are able to bind eIF4E in vitro can induce cell death even though they have very different sequences outside their common eIF4E-binding motif (FIG. 12a). In addition, peptides harbouring single or triple alanine substitutions at conserved residues important in binding to eIF4E either had no significant effect on cell survival or a reduced ability to induce cell death. Taken together with the in vitro binding studies, these data underpin a strong structure/activity relationship and thus provide strong evidence that eIF4E-binding peptides induce cell death through their interaction with eIF4E.

During eIF4E-binding peptide-induced cell death, cells shrank and underwent blebbing, two characteristics of apoptosis (FIG. 14a). To investigate whether eIF4E-binding peptide-induced cell death also caused nuclear condensation and DNA cleavage, other characteristics associated with apoptosis, a number of methodologies were employed. FACS analysis of propidium iodide-stained MRC5 cells treated with the Hu4G peptide revealed a shift in the DNA profile from G0/1 to sub G0/1, indicating cell death and possible chromosomal DNA fragmentation/condensation (FIG. 14b). DNA fragmentation was confirmed using TdT-mediated dUTP nick end labelling (TUNEL) (FIG. 14c). Analysis of the cell nuclei by DAPI staining revealed that the cells incubated with the Hu4G presented signs of nuclear condensation, either having condensed nuclei or nuclei with a punctate appearance (FIG. 14d).

An early event considered decisive in apoptosis is the opening of the mitochondrial permeability transition (MPT) pore (20–22). To characterise further the eIF4E-binding peptide-induced cell death, the development of the MPT was investigated in living MRC5 cells loaded with the fluorescent dye, JC1 (21). No changes in florescence were observed upon the addition of the inactive Hu4G YLL-AAA peptide (FIG. 14e). In contrast, addition of the Hu4G peptide led to a rapid increase (within 5 min) in the intensity of the green fluorescence concomitantly with a loss of orange fluorescence indicative of a drop in Ψm within the mitochondria due to the MPT pore opening (FIG. 14e).

During apoptosis a conserved family of aspartic acid-specific cysteine proteases or caspases are frequently activated (23). However no such activation was detected in eIF4E-binding peptide-induced cell death (results not shown). Moreover, pre-treatment of the MRC5 cells with ZVAD.fmk, a wide spectrum caspase inhibitor, did not affect peptide-induced cell death (results not shown). Therefore, eIF4E-binding peptide-induced cell death appears not to involve caspase activation. Taken together, these data provide evidence that eIF4E peptide-induced cell death in MRC5 cells proceeds through a caspase-independent mechanism which exhibits a number of features observed in apoptosis. The rapidity with which the cells die and apparent lack of caspase activation are not features associated with classical apoptosis. However, it is clear that the activation of caspases is not a prerequisite for apoptosis (24,25). For example, it has been reported that mitochondrial associated protein, apoptosis inducing factor (AIF), can induce rapid caspase-independent apoptosis (26). The effect of these eIF4E-binding peptides on cell survival was also tested on a number of other cell-types including HaCaT, Swiss 3T3, RATI and HeLa cells. In all of cases, addition of the Hu4G peptide resulted in rapid cell death whereas the Hu4G YLL-AAA peptide had no effect on cell survival (results not shown). However, characterisation of the cell death process in these cells was not investigated in detail.

In the presence of 10% ECS, cells were resistant to treatment with 20 μm of the peptides. Cells only died if they were serum deprived for 72 hours (more than 85%) within 15 minutes after the peptide had been applied (see FIG. 15). However, if serum deprived cells (72 h) were pre-treated with 10% FCS or with 20 nM PMA (phorbol ester) for 15 minutes before the peptides were added, the cells survived the subsequent peptide treatment (60–70%).

Furthermore, if the serum deprived cells were instead pre-treated with the MAPK inhibitor PD098059 for 1 hour before 10% FCS was added, approximately 80–90% of the cells died. This result shows that cell death is linked to a genetic program and that the cells can be rescued from peptide induced death by addition of FCS or PMA. It is also suggested by the speed with which the cells died after peptide treatment and the rapid rescue by FCS or PMA and the effect of the MAPK inhibitor, that the effect of the peptides on cell death is dependent on secondary modifications in the cells.

Serum deprived cells were treated with the general translation inhibitors Cyclohexamide or Pactamycin at indicated concentrations or the H4G peptide in the presence of 35S-Met for 30 minutes (see FIGS. 16a,b). Cells were lysed and the amount of translation was estimated by counting incorporated 35S-Met in precipitated protein fractions. As expected, the peptide treated cells do not incorporate 35S-Met and they die. However, general translation inhibitors block translation but they do not kill the cells.

It remained possible that eIF4E-binding peptide-induced cell death involved the up- or down-regulation of the translation of a specific mRNA or subset of mRNAs. To investigate this, MRC5 cells were treated with cycloheximide or pactamycin to prevent ongoing protein synthesis prior to the addition of the Hu4G peptide. However, this did not result in any protection against the effect of the Hu4G peptide (FIG. 16c). These data show that continued translation is not required for the peptides to induce cell death, and thus provides evidence that the up- or down-regulation of the translation of a specific mRNA(s) does not mediate eIF4E-binding peptide-induced cell death.

In another experiment, cells that were serum deprived for 72 hours and pre-treated with general translation inhibitors were shown to be just as susceptible to cell death (85%) as cells not treated with translation inhibitors. This strongly indicates that the effect of cell killing by the peptides is not mediated by inhibition of translation and is therefore not mediated by a translation product. This observation is very surprising and novel.

The present data thus indicate that eIF4E plays a direct role in controlling cell survival that is not linked to its known role in regulating mRNA translation. It is presently not clear what mechanism underlies this eIF4E-binding peptide-induced cell death. Without wishing to be bound by theory it is possible that it is associated with a yet undefined function of eIF4E. Recently, it has been reported that eIF4E co-localises in the nucleus with splicing factors and eIF4E may therefore play an additional role in splicing or RNA export (27). As penetratin-linked peptides can enter all compartments of the cell it is possible that these peptides interfere with a nuclear function of eIF4E which results in cell death. However, it is also possible that deleterious perturbations in eIF4E function may directly trigger the apoptotic machinery. This could be a "checkpoint" mechanism by which the cells sense the integrity of the translation machinery. Indeed, the rapidity of cell death suggests that binding of the peptides to eIF4E may directly signal the induction of cell death.

In conclusion, the present data clearly indicates that eIF4E plays a critical role in cell survival, which may be related to its known role in cell transformation. However, its role in cell survival appears to involve a novel mechanism independent of its known function in mRNA translation.

REFERENCES

1. Sonenberg, N. & Gingras, A. The mRNA 5' cap-binding protein eIF4E and control of cell growth. *Curr Opin Cell Biol* 10, 268–75 (1998).
2. Hentze, M. EIF4G: a multipurpose ribosome adapter? *Science* 275, 500–1 (1997).
3. Pyronnet, S. et al. Human eukaryotic translation initiation factor 4G(eIF4G) recruits mnk1 to phosphorylate eIF4E. *EMBO J.* 18, 270–9 (1999).
4. Lawrence Jr, J. & Abraham, R., R. PHAS/4E-BPs as regulators of mRNA translation and cell proliferation. *Trends Biochem Sci* 22, 345–9 (1997).
5. Rousseau, D., Gingras, A., Pause, A. & Sonenberg, N. The eIF4E-binding proteins 1 and 2 are negative regulators of cell growth. *Oncogene* 13, 2415–20 (1996).
6. Flynn, A. & Proud, G. Insulin-stimulated phosphorylation of initiation factor 4E is mediated by the MAP kinase pathway. *FEBS Lett* 389, 162–6 (1996).
7. Rosenwald, I., Laxaris-Karatzas, A., Sonnenberg, N. & Schxnidt, E. Elevated levels of cyclin D1 protein in response to increased expression of eukaryotic initiation factor 4E. *Mol Cell Biol* 13, 7358–63 (1993).
8. Shantz, L., Hu. R. & Pegg, A. Regulation of ornithine decarboxylase in a transformed cell line that overexpresses translation initiation factor eIF-4E. *Cancer Res* 56, 3265–9 (1996).
9. Li, B., Liu, L., Dawson, M. & De Benedetti, A. Overexpression of eukaryotic initiation factor 4E(eIF4E) in breast carcinoma. *Cancer* 79, 2385–90 (1997).
10. Rosenwald, J. B. et al. Upregulation of protein synthesis initiation factor eIF4E is an early event during colon carcinogenesis. *Oncogene* 18, 2507–2517 (1999).
11. Li, B., McDonald, J., Nassar, R. & De Beneditte, A. Clinical outcome in stage I to III breast carcinoma and eIF4E overexpression. *Ann Surg* 227, 756–61; discussion 761–3 (1998).
12. Nathan, C. et al. Detection of the proto-oncogene eIF4E in surgical margins may predict recurrence in head and neck cancer. *Oncogene* 15, 579–84 (1997).
13. De Benedetti, A. & Rhoads, R. Overexpression of eukaryotic protein synthesis initiation factor 4E in HeLa cells results in aberrant growth and morphology. *Proc Natl Acad Sci USA* 87, 8212–6 (1990).
14. Fukuchi-Shimogori, T. et al. Malignant transformation by overproduction of translation initiation factor eIF4G. *Cancer Res* 57, 5041–4 (1997).
15. Polunovsky, V. et al Translation control of programmed cell death: eukaryotic translation initiation factor 4E blocks apoptosis in growth-factor-restricted fibroblasts with physiologically expressed or deregulated *Myc. Mol Cell Biol* 16, 6573–81 (1996).
16. Fletcher, C. et al, 4E binding proteins inhibit the translation factor without folded structure. *Biochemistry* 37, 9–15 (1998).
17. Lawrence Jr, J. & Abraham, R. PHAS/4E-BPs as regulators of mRNA translation and cell proliferation. *Trends Biochem Sci* 22, 345–9 (1997).
18. Rousseau, D., Gingras, A., Pause, A. & Sonenberg, N. The eIF4E-binding proteins 1 and 2 are negative regulators of cell growth. *Oncogene* 13, 2415–20 (1996).
19. Sonenberg, N. & Gingras, A. The mRNA 5' cap-binding protein eTF4E and control of cell growth. *Curr Opin Cell Biol* 10, 268–75 (1998).
20. Green, D. R., Reed, J. C. Mitochondria and apoptosis. *Science* 1998. 281; 1309–1312.
21. Kroemer, G: The proto-oncogene Bcl-2 and its role in regulating apoptosis. *Nat Med* 1997. 3; 614–620.
22. Minamikawa, T., Williams, D. A., Bowser, D. N., Nagley, P: Mitochondrial permeability transition and swelling can occur reversibly without inducing cell death in intact human cells. *Exp Cell Res* 1999. 246; 26–37.
23. Wolf, B. B., Green, D. R: Suicidal tendencies: apoptotic cell death by caspase family proteinases. *J Biol Chem* 1999. 274; 20049–20052.
24. Okuno, S., Shimizu, S., Ito, T., Nomura, M., Hamada, E., Tsujimoto, Y., Matsuda, H: Bcl-2 prevents caspase-independent cell death. *J Biol Chem* 1998. 273; 34272–34277.
25. Xiang, J., Chao, D. T., Korsmeyer, S. J: BAX-induced cell death may not require interleukin 1 beta-converting enzyme-like proteases. *Proc Natl Acad Sci USA* 1996. 93; 14559–14563.
26. Susin, S. A., Lorenzo, H. K., Zamzami, N., Marzo, I., Snow, B. E., Brothers, G. M., Mangion, J., Jacotot, E., Costantini, P., Loeffler, M., Larochette, N., Goodlett, D. R., Aebersold, R., Siderovski, D. P., Penninger, J. M., Kroemer, G: Molecular characterization of mitochondrial apoptosis-inducing factor. *Nature* 1999. 397; 441–446.
27. Dostie, J., Lejbkowicz, F., Sonenberg, N: Nuclear Eukaryotic Initiation Factor 4E (eIF4E) Colocalizes with Splicing Factors in Speckles. *J Cell Biol* 2000. 148; 239–246.

The invention claimed is:

1. A therapeutic method of inducing programmed cell death, said method comprising administering to a recipient a peptide of 10–25 amino acids, comprising the sequence: (KR)xxYxxx(F/Q)L(L/M) (SEQ ID NO:5), wherein x is any amino acid.

2. The method according to claim 1, wherein said peptide comprises the sequence:
   KKRYDREFLLGF (SEQ ID NO:1);
   RVRYSRDOLLDL (SEQ ID NO:2); or
   RIIYDRKFL(L/M) (SEQ ID NO:3).

3. The method according to claim 1, wherein said method induces cell death in tumour cells.

4. A method of inducing programmed cell death, said method comprising administering to a recipient a peptide of 10–25 amino acids in length, comprising the sequence:
   (K/R) xxYxxx (F/Q) L (L/M) (SEQ ID NO:5),
   wherein x is any amino acid, a synthetic amino acid or an unnatural amino acid.

5. A method of inducing programmed cell death in tumour cells, said method comprising administering to a recipient a peptide of 10–25 amino acids in length, comprising the sequence:
   (K/R) xxYxxx (F/Q) L (L/M) (SEQ ID NO:5),
   wherein x is any amino acid, a synthetic amino acid or an unnatural amino acid.

* * * * *

UNITED STATES PATENT AND TRADEMARK OFFICE
CERTIFICATE OF CORRECTION

| | | |
|---|---|---|
| PATENT NO. | : 7,141,541 B1 | Page 1 of 1 |
| APPLICATION NO. | : 10/019198 | |
| DATED | : November 28, 2006 | |
| INVENTOR(S) | : Proud et al. | |

It is certified that error appears in the above-identified patent and that said Letters Patent is hereby corrected as shown below:

Column 21,
Line 5 should read -- (KR)xxYxxx(F/Q)L(L/M)(SEQ ID NO:5), wherein x is any --

Signed and Sealed this

Thirty-first Day of July, 2007

JON W. DUDAS
*Director of the United States Patent and Trademark Office*